United States Patent [19]

Miyamoto et al.

[11] Patent Number: 4,971,970
[45] Date of Patent: Nov. 20, 1990

[54] BENZOHETEROCYCLIC COMPOUNDS

[75] Inventors: Hisashi Miyamoto; Hiroshi Yamashita, both of Tokushima; Michiaki Tominaga, Tokushima; Yoichi Yabuuchi, Tokushima, all of Japan

[73] Assignee: Otsuka Pharmaceutical Company, Limited, Tokyo, Japan

[21] Appl. No.: 424,501

[22] Filed: Oct. 20, 1989

[30] Foreign Application Priority Data

Oct. 20, 1988 [JP] Japan .................................. 63-265830
Sep. 12, 1989 [JP] Japan .................................. 64-236642

[51] Int. Cl.⁵ .................... A61K 31/495; C07D 401/04
[52] U.S. Cl. ...................................... 514/254; 544/363
[58] Field of Search ......................... 544/363; 514/254

[56] References Cited

U.S. PATENT DOCUMENTS 4,620,007 10/1986 Grohe et al. .......................... 544/363
4,705,788 11/1987 Schriewer et al. ................... 544/363

Primary Examiner—Richard L. Raymond
Assistant Examiner—James H. Turnipseed
Attorney, Agent, or Firm—Wegner, Cantor, Mueller & Player

[57] ABSTRACT

Novel 3-formyl-4-oxoquinoline compounds of the formula:

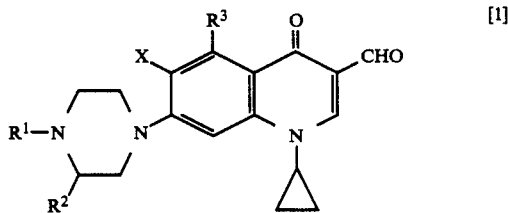

wherein $R^1$ is hydrogen atom or a lower alkanoyl, $R^2$ is hydrogen atom or a lower alkyl, $R^3$ is a lower alkyl, and X is halogen, and pharmaceutically acceptable salts thereof, said compounds having excellent antimicrobial activity and hence being useful as an antimicrobial agent, and a pharmaceutical composition containing said compound as an active ingredient.

16 Claims, No Drawings

BENZOHETEROCYCLIC COMPOUNDS

The present invention relates to novel antimicrobial benzoheterocyclic compounds of the formula [1]:

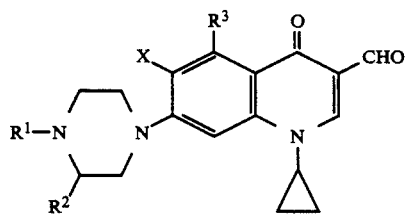

wherein $R^1$ is hydrogen atom or a lower alkanoyl group, $R^2$ is hydrogen atom or a lower alkyl group, $R^3$ is a lower alkyl group, and X is a halogen atom, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

PRIOR ART

Kondo et al., J. Med. Chem., 1988, 31, 221–225 disclose synthetic and antimicrobial activity of 3-formylquinolone derivatives of the formula:

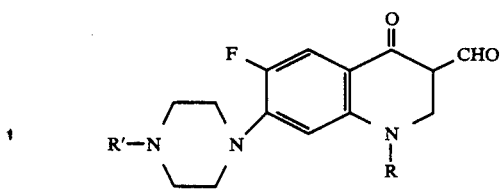

wherein R is ethyl or cyclopropyl and R' is H or methyl, which are similar to the compounds of the present invention, but they are different particularly in the absence of an alkyl substituent at the 5-position of the quinolone nucleus.

British Patent Publication 2,188,317-A discloses 1-cyclopropyl-3-quinoline carboxylic acid derivatives having antibacterial activities of the formula:

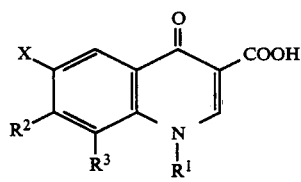

wherein $R^1$ is a substituted or unsubstituted cyclopropyl, $R^2$ is a 5- to 9-membered saturated or unsaturated heterocyclic group including a substituted or unsubstituted piperazinyl group, $R^3$ is a substituted or unsubstituted lower alkyl group, and X is a halogen atom.

BRIEF DESCRIPTION OF THE INVENTION

The object of the present invention is to provide novel benzoheterocyclic compounds of the formula [1] and salts thereof which have excellent antimicrobial activity. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the specification, the term "a halogen atom" includes fluorine, chlorine, bromine or iodine atom.

The term "a lower alkyl" includes straight chain or branched chain $C_1$-$C_6$ alkyl, such as methyl, ethyl, propyl, isopropyl, butyl, tert-butyl, pertyl, hexyl, etc.

The term "a lower alkanoyl" includes a straight chain or branched chain $C_1$-$C_6$ alkanoyl, such as formyl, acetyl, propionyl, butyryl, pentanoyl, hexanoyl, etc.

The compounds of the present invention of the above formula [1] can be prepared by various processes and preferably prepared, for example, by the processes as shown in the following reaction schemes.

[Reaction scheme-I]

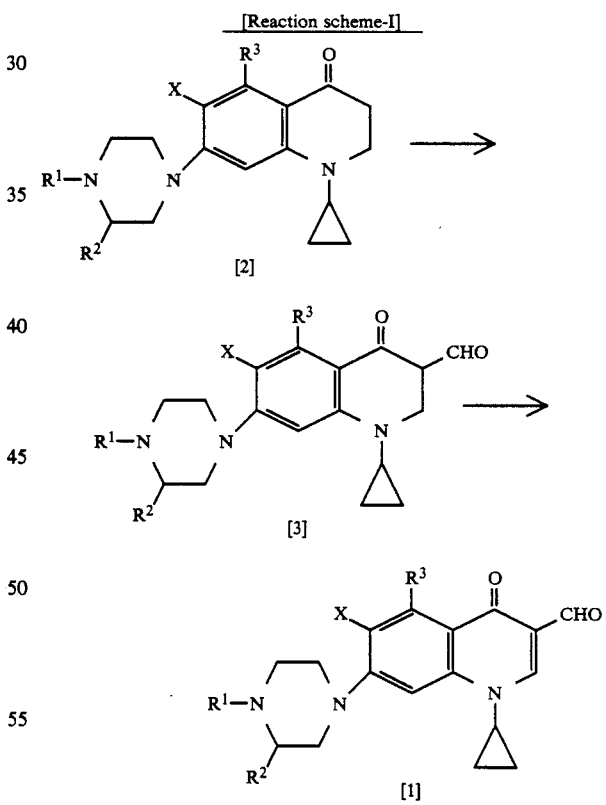

wherein $R^1$, $R^2$, $R^3$ and X are as defined above.

The reaction of converting the compound [2] into the compound [3] can be carried out by reacting the compound [2] with a formic acid ester in an appropriate solvent in the presence of a basic compound. The formic acid ester includes, for example, lower alkyl formates, such as methyl formate, ethyl formate, propyl formate, butyl formate, etc. The formic acid ester is used in an amount of at least 1 mole, preferably 1 to 10 moles, to 1 mole of the compound [2]. The solvent includes halogenated hydrocarbons (e.g. dichloromethane, dichloroethane, chloroform, etc.), aromatic hydrocarbons (e.g. benzene, toluene, xylene, etc.), ethers (e.g. dimethoxyethane, tetrahydrofuran, diethyl ether, etc.), esters (e.g. ethyl acetate, methyl acetate, etc.), ketones (e.g. acetone, etc.), aprotic polar solvents (e.g. dimethylformamide, dimethylsulfoxide, hexamethylphosphoric triamide, etc.), alcohols (e.g. methanol, ethanol, propanol, butanol, 3-methoxy-1-butanol, ethyl cellosolve, methyl cellosolve, etc.), pyridine, acetonitrile, or a mixture of these solvents. The basic compound includes, for example, organic bases such as triethylamine, trimethylamine, pyridine, dimethylaniline, N-methylmorpholine, 1,5-diazabicyclo[4.3.0]nonene-5 (DBN), 1,8-diazabicyclo[5.4.0]-undecene-7 (DBU), 1,4-diazabicyclo[2.2.2]octane (DABCO), and the like, and inorganic bases such as potassium carbonate, sodium carbonate, potassium hydrogen carbonate, sodium hydrogen carbonate, sodium hydroxide, potassium hydroxide, sodium hydride, potassium hydride, silver carbonate, alcoholates (e.g. sodium methylate, sodium ethylate, etc.), and the like. The above reaction is usually carried out at a temperature of from room temperature to about 150° C, preferably from room temperature to about 100° C, for about 1 to 5 hours.

In the case of the compound of the formula [2] wherein $R^1$ is hydrogen atom, when the reaction is carried out under the above conditions, formylation proceeds simultaneously to produce a compound of the formula [3] wherein $R^1$ is formyl, but this product can easily be removed from the reaction mixture.

The reaction of converting the compound [3] into the compound [1] is carried out in a suitable solvent in the presence of an oxidizing agent. The oxidizing agent includes, for example, benzoquinones (e.g. 2,3-dichloro-5,6-dicyanobenzoquinone, chloranil (i.e. 2,3,5,6-tetrachlorobenzoquinone), etc.), halogenating agents (e.g. N-bromosuccinimide, N-chlorosuccinimide, bromine, etc.), metal oxides (e.g. active selenium dioxide, manganese dioxide, etc.), hydrogenation catalysts (e.g. palladium-carbon, palladium black, palladium oxide, Raney nickel, etc.), and the like. The amount of the oxidizing agent is not specified but is selected from a wide range of amount, and it is usually used in an amount of about 1 to 15 mole, preferably about 1 to 10 moles, to 1 mole of the compound [3]. When a hydrogenation catalyst is used as the oxidizing agent, it is usually used in a catalytic amount. The solvent includes ethers (e.g. dioxane, tetrahydrofuran, methoxyethanol, dimethoxymethane, etc.), aromatic hydrocarbons (e.g. benzene, toluene, xylene, etc.), halogenated hydrocarbons (e.g. dichloromethane, dichloroethane, chloroform, carbon tetrachloride, etc.), alcohols (e.g. methanol, ethanol, butanol, amyl alcohol, hexanol, etc.), protic polar solvents (e.g. acetic acid, etc.), aprotic polar solvents (e.g. dimethylformamide, dimethylsulfoxide, hexamethylphosphoric triamide, etc.) The reaction is usually carried out at a temperature of from room temperature to about 150° C., preferably from room temperature to about 100° C., for about 1 to 10 hours.

The compound of the formula [1] wherein $R^1$ is a lower alkanoyl group can be converted into the compound of the formula [1[ wherein $R^1$ is hydrogen atom by hydrolysis thereof. The hydrolysis can be effected under the same conditions as used in a conventional hydrolysis. Specifically, it is carried out in the presence of a basic compound (e.g. sodium hydroxide, potassium hydroxide, barium hydroxide, potassium carbonate, etc.), a mineral acid (e.g. sulfuric acid, hydroxhloric acid, nitric acid, etc.) or an organic acid (e.g., acetic acid, aromatic sulfonic acids, etc.) in a suitable solvent such as water, alcohols (e.g. methanol, ethanol, isopropanol, etc.), ketones (acetone, methyl ethyl ketone, etc.), ethers (e.g. dioxane, ethyleneglycol diethyl ether, etc.), actic acid, or a mixture thereof. The reaction is usually carried out at a temperature of from room temperature to about 200° C., preferably from room temperature to about 150° C., for about 0.1 to 30 hours.

The starting compound [2[ used in the above Reaction Scheme-I can be prepared, for example, by the process as shown in the following Reaction Scheme-II.

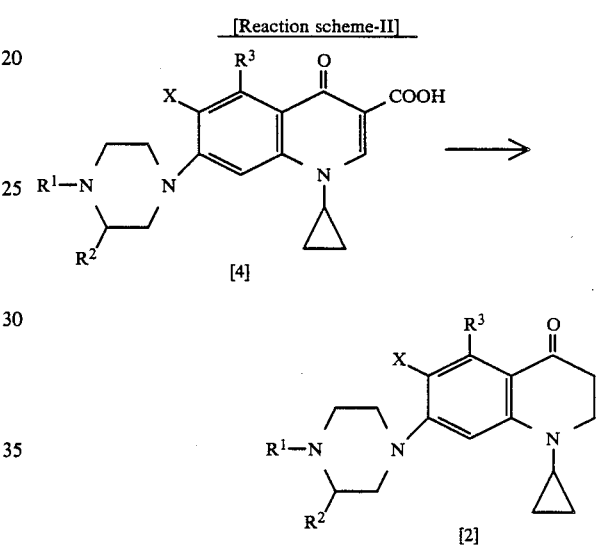

wherein $R^1$, $R^2$, $R^3$ and X are as defined above.

The reaction of converting the compound [4] into the compound [2] is carried out in a suitable solvent in the presence of a hydrogenation reducing agent. The reducing agent includes, for example, sodium borohydride, and the like. The reducing agent is usually used in an amount of at least 1 mole, preferably about 1to 10 moles, to 1 mole of the compound [4]. The solvent includes, for example, water, lower alcohols (e.g. methanol, ethanol, isopropanol, etc.), ethers (e.g. tetrahydrofuran, diethyl ether, diglyme, etc.), and the like. The reaction is usually carried out at a temperature of from about 0° to 70° C., preferably from about 0° C. to 50° C., for about 10 minutes to about 5 hours.

The compound [4] can be prepared by various processes, for example, by the processes as shown in the following Reaction Schemes-III and -IV.

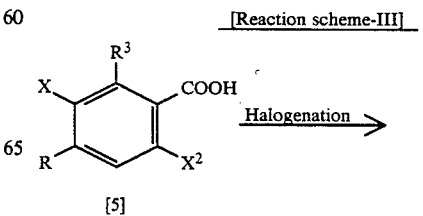

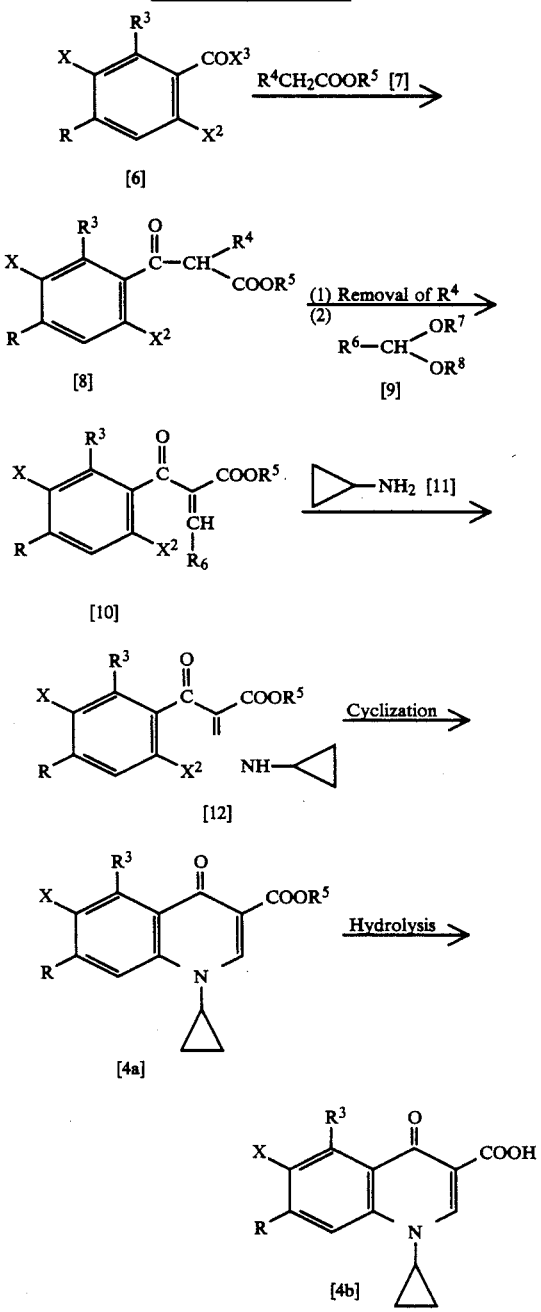

[Reaction scheme-III]

wherein $R^3$ and X are as defined above, R is a halogen atom or the group of the formula:

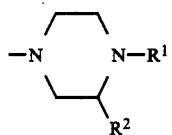

(wherein $R^1$ and $R^2$ are as defined above), $R^4$ is a group of the formula: $-COR^9$ (wherein $R^9$ is a lower alkyl) or a group of the formula: $-COOR^{10}$ (wherein $R^{10}$ is a lower alkyl), $R^5$ is a lower alkyl, $R^6$ is a group of the formula:

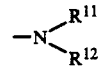

(wherein $R^{11}$ and $R^{12}$ are each a lower alkyl) or a lower alkoxy, $X^2$ and $X^3$ are each a halogen atom, $R^7$ and $R^8$ are each a lower alkyl.

The halogenation of the compound [5] is carried out by reacting with a halogenating agent in the presence or absence of a solvent. The solvent includes aromatic hydrocarbons (e.g. benzene, toluene, xylene, etc.), halogenated hydrocarbons (e.g. dichloromethane, chloroform, carbon tetrachloride, etc.), ethers (e.g. dioxane, tetrahydrofuran, diethyl ether, etc.), dimethylformamide (DMF), dimethylsulfoxide (DMSO), and the like. The halogenating agent may be any conventional halogenating agents which can convert hydroxy in a carboxy group into a halogen atom, and includes, for example, thionyl chloride, phosphorus oxychloride, phosphorus oxybromide, phosphorus pentachloride, phosphorus pentabromide, and the like. The amounts of the compound [5] and the halogenating agent are not particularly limited, but, in the case of using no solvent, the halogenating agent is usually used in a large excess amount, and in the case of using a solvent, the halogenating agent is usually used in an amount of at least 1 mole, preferably 2 to 4 moles, per 1 mole of the compound [5]. The reaction temperature and the reaction period of time are not particularly limited either, but the reaction is usually carried out at a temperature of from room temperature to about 100° C. for about 30 minutes to about 6 hours.

The reaction between the compound [6] and the compound [7] is carried out in a suitable solvent in the presence of a basic compound. The solvent used in the reaction may be any conventional solvents unless they give any undesirable effect on the reaction, and includes, for example, water, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, hexamethylphosphoric triamide (HMPA), etc.), and a mixture of these solvents. The basic compound employed in the reaction includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), and organic bases (e.g. pyridine, piperidine, quinoline, triethylamine, N,N-dimethylaniline, etc.). The reaction is usually carried out at a temperature of from about 0° to 150° C., preferably from about 0° to 120° C., for about 0.5 to 20 hours. The compound [7] is usually used in an amount of at least 1 mole, preferably 1 to 2 moles, per 1 mole of the compound [6]. The basic compound is usually used in an amount of at least 1 mole, preferably 1 to 2 moles, per 1 mole of the compound [6].

The compound [8] wherein $R^4$ is the group of the formula: $-COR^9$ is subjected to the reaction for removal of the group: $-COR^9$ in a suitable solvent in the presence of a basic compound. The solvent used in the reaction includes, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. DMF, DMSO, HMPA, etc.), and the like. The basic compound includes ammonia gas, aqueous ammonia, ammonium salts (e.g. ammonium chloride, etc.), primary or secondary amines (e.g. ethylamine, diethylamine, piperidine, etc.), and the like. The reaction is usually carried out at a temperature of from about 0° to 150° C., preferably from room temperature to about 100° C., for about 1 to 20 hours The compound [8] wherein $R^4$ is a group of the formula: -COOR$^{10}$ is subjected to the reaction for removal of the group: -COOR$^{10}$ in an aqueous solution in the presence of an acid catalyst. The acid catalyst used in the reaction includes mineral acids (e.g. hydrochloric acid, sulfuric acid, etc.) and organic acids (e.g. p-toluenesulfonic acid, etc.). The reaction is usually carried out at a temperature of from about 0° to 150° C., preferably from room temperature to about 100° C., for about 1 to 20 hours.

The reaction between the obtained $R^4$ group-removed compound and the compound [9] is carried out in a suitable solvent. The solvent employed in the reaction may be any solvents which are used in the above reaction for the removal of the $R^4$ group in addition to anhydrous lower alkanoic acid such as acetic anhydride. The reaction is usually carried out at a temperature of from about 0° to 200° C., preferably from about 0° to 150° C., for about 0.5 to 10 hours. The compound [9] is usually used in an equimolar to large excess amount, preferably in an amount of 1 to 2 moles to 1 mole of the compound [8]. In case of using a compound [9] wherein $R^6$ is a lower alkoxy group, the reaction may also be carried out by using acid anhydrides such as acetic anhydride as a solvent as well as the abovementioned solvents at a temperature of from about 0° to 200° C., preferably from about 0° to 170° C.

The reaction between the compound [10] and the compound [11] is carried out in a suitable solvent. The solvent employed in the reaction may be any conventional solvents unless they give any undesirable effect on the reaction, and includes, for example, alcohols (e.g. methanol, ethanol, propanol, etc.), ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The reaction is usually carried out at a temperature of from about 0° to 150° C., preferably from room temperature to about 100° C., for about 0.1 to 15 hours. The compound [11] is usually used in an amount of at least 1 mole, preferably 1 to 2 moles, per 1 mole of the compound [10]. In the reaction, a basic compound may optionally be added. Such basic compound may be any basic compounds which are used in the above reaction between the compound [6] and the compound [7].

The cyclization of the compound [12] is carried out in a suitable solvent in the presence of a basic compound. The solvent employed in the reaction may be any conventional solvents unless they give any undesirable effect on the reaction, and includes, for example, ethers (e.g. diethyl ether, dioxane, tetrahydrofuran, monoglyme, diglyme, etc.), aliphatic hydrocarbons (e.g. n-hexane, heptane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The basic compound employed in the reaction includes inorganic bases (e.g. metallic sodium, metallic potassium, sodium hydride, sodium amide, sodium hydroxide, potassium hydroxide, sodium carbonate, potassium carbonate, etc.), metal alcoholates (e.g. sodium methylate, sodium ethylate, etc.), organic bases (e.g. 1,8-diazabicyclo[5.4.0]undecene-7 (DBU), N-benzyltrimethylammonium hydroxide, tetrabutylammonium hydroxide, etc.), and the like. The reaction is usually carried out at a temperature of from about 0° to 200° C., preferably from room temperature to about 150° C., for about 0.5 to 15 hours. The basic compound is usually used in an amount of at least 1 mole, preferably 1 to 2 moles, per 1 mole of the compound [12].

The hydrolysis of the compound [4a] can be carried out under the same conditions as in the reaction of converting the compound of the formula [1] wherein $R^1$ is a lower alkanoyl group to the compound of the formula [1] wherein $R^1$ is hydrogen atom.

[Reaction Scheme-IV]

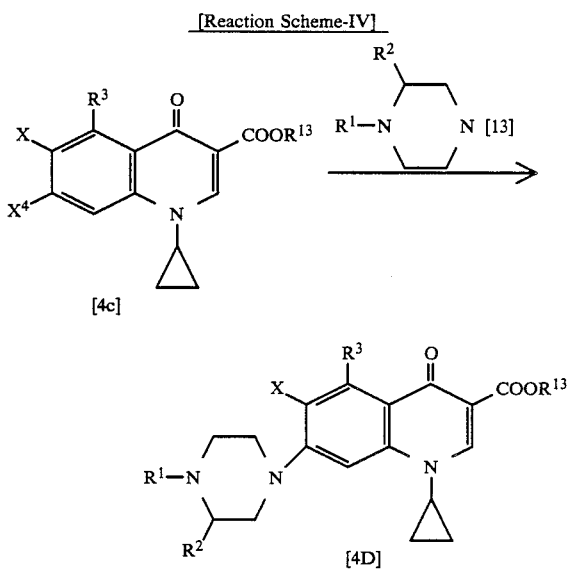

wherein $R^1$, $R^2$, $R^3$ and X are as defined above, $X^4$ is a halogen atom, and $R^{13}$ is hydrogen atom or a group of the formula:

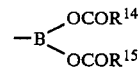

(wherein $R^{14}$ and $R^{15}$ are each an alkyl).

For conducting the reaction between the compound [4c] and the compound [13], both compounds are used in a wide range of ratios, and the compound [13] is usually used in an amount of at least 1 mole, preferably about 1 to 5 moles, per 1 mole of the compound [4c]. The reaction is carried out in an inert solvent, which includes, for example, water, alcohols (e.g. methanol, ethanol, isopropanol, butanol, amyl alcohol, isoamyl alcohol, etc.), aromatic hydrocarbons (e.g. benzene, toluene, xylene, etc.), ethers (e.g. tetrahydrofuran, dioxane, diglyme, etc.), dimethylacetamide, DMF, DMSO, HMPA, N-methylpyrrolidone, and the like and a mixture thereof. Among these solvents, the preferred one is DMF, DMSO, HMPA, and N-methylpyrrolidone. The reaction may also be carried out in the presence of an acid-removing agent, including inorganic carbonates (e.g. sodium carbonate, potassium carbonate, sodium hydrogen carbonate, potassium hydrogen carbonate, etc.) and organic bases (e.g. pyridine, quinoline, triethylamine, etc.). An alkaline metal halide such as potassium fluoride may also be added to the reaction mixture. The reaction is usually carried out under a pressure of from 1 to 20 atm., preferably from 1 to 10 atm., at a temperature of from room temperature to about 250° C., preferably from room temperature to about 200° C., for about 10 minutes to about 30 hours.

The compound [4d] wherein $R^{13}$ is a group of the formula:

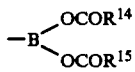

can be converted into the corresponding compound [4d] wherein $R^{13}$ is hydrogen atom by treating the former compound with an acid or a base to decompose the chelate compound. The acid employed in the reaction includes mineral acids (e.g. hydrochloric acid, sulfuric acid, etc.) and organic acids (e.g. acetic acid, p-toluenesulfonic acid, etc.). The base employed in the reaction includes inorganic bases (e.g. sodium hydroxide, potassium hydroxide, sodium hydrogen carbonate, potassium hydrogen carbonate, potassium carbonate, etc.) and organic bases (e.g. triethylamine, etc.). The reaction favorably proceeds at a temperature of from about 0° to 150° C., preferably from about 0° to 100° C. The acid or the base may be used in an amount of at least 1 mole, preferably 1 to 10 moles, per 1 mole of the starting compound.

The compound [1 of the present invention can easily be converted into a salt thereof by treating with a pharmaceutically acceptable acid or base. The acid includes inorganic acids such as hydrochloric acid, sulfuric acid, phosphoric acid and hydrobromic acid and organic acids such as oxalic acid, maleic acid, fumaric acid, malic acid, tartaric acid, citric acid, benzoic acid, lactic acid, methanesulfonic acid and propionic acid. The base includes sodium hydroxide, potassium hydroxide, calcium hydroxide, sodium carbonate, potassium hydrogen carbonate, and the like.

The compound thus obtained can easily be isolated and purified by conventional methods, such as, for example, extraction with solvents, dilution method, recrystallization, column chromatography and preparative thin layer chromatography.

The compounds of the present invention include also stereo isomers and optically active isomers thereof.

The compounds or their salts of the present invention show an excellent antimicrobial activity against mycoplasma, *Pseudomonas aeruginosa*, anaerobic bacteria, resistant cells against various antimicrobials, clinically isolated bacteria, and gram negative and gram positive bacteria such as *Enterococcus faecalis* and *Staphylococcus pyogenes* and hence are useful as an antimicrobial agent for the treatment of diseases induced by these microorganisms. These compounds also show low toxicity and less side effect and are characteristic in good absorbability and in sustained activity. Moreover, the compounds are highly excreted via urine and hence are useful for the treatment of urinary infectious diseases, and because of good migration into lung tissue, they are useful for the treatment of respiratory infectious diseases, and further because of easy excretion via bile, they are also useful for the treatment of intestinal infectious diseases.

Among the compounds [1] of the present invention, the preferable ones are the compounds wherein X is chlorine or fluorine atom, most preferably fluorine atom, and $R^3$ is methyl or ethyl, most preferably methyl.

The absorbability of the compounds of the present invention in the living body can be increased by converting them into the corresponding salt such as, for example, lactate or hydrochloride.

The compounds of the present invention are usually used in the form of a usual pharmaceutical preparation. The pharmaceutical preparation can be prepared in admixture with conventional pharmaceutically acceptable diluents or carriers, such as fillers, bulking agents, binding agents, wetting agents, disintegrators, surfactants and lubricating agents. The pharmaceutical preparation includes various preparations suitable for treatment of the diseases, for example, tablets, pills, powders, solutions, suspensions, emulsions, granules, capsules, suppositories, injections such as solutions and suspensions, and the like. In the preparation of tablets, there may be used any conventional carriers, for example, excipients such as lactose, white sugar, sodium chloride, glucose, urea, starches, calcium carbonate, kaolin, crystalline cellulose and silicate, binding agents such as water, ethanol, propanol, simple syrup, glucose solution, starch solution, gelatin solution, carboxymethyl cellulose, shellac, methyl cellulose, potassium phosphate and polyvinylpyrrolidone, disintegrators such as dry starch, sodium alginate, agar powder, laminaran powder, sodium hydrogen carbonate, calcium carbonate, polyoxyethylene sorbitan fatty acid esters, sodium laurylsulfate, stearic monoglyceride, starches and lactose, disintegration inhibitors such as white sugar, stearin, cacao butter and hydrogenated oils, absorption promoters such as quaternary ammonium salts and sodium laurylsulfate, wetting agents such as glycerin and starches, adsorbents such as starches, lactose, kaolin, bentonite and colloidal silicates, lubricants such as purified talc, stearates, boric acid powder and polyethylene glycol, and the like. The tablets may also be coated with conventional coating agents, for example, may be in the form of a sugar coated tablet, a gelatin-coated tablet, an enteric coating tablet, a film coating tablet, or a double or multiple layer tablet. In the preparation of pills, there may be used conventional carriers, including excipients such as glucose, lactose, starches, cacao butter, hydrogenated vegetable oils, kaolin and talc, binding agents such as gum arabic powder, tragacanth powder, gelatin and ethanol, disintegrators such as laminaran and agar, and the like. In the preparation of suppositories, there may be used conventional carriers, such as polyethylene glycol, cacao butter, higher alcohols, higher alcohol esters, gelatin and semi-synthetized glycerides. In the preparation of injections, the solutions, emulsions or suspensions of the compounds are sterilized and are preferably made isotonic with the blood. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol or polyoxyethylene sorbitan fatty acid esters. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweetening agents, and other medicaments. The preparations in the form of a paste, cream or gel may be prepared by using as a diluent white vaseline, paraffin, glycerin, cellulose derivatives, polyethylene glycol, silicone, bentonite, or the like. When the compound of the active ingredient precipitates in the injection, an acid such as methanesulfonic acid, propionic acid, hydrochloric acid, succinic acid or lactic acid may optionally be added to the injection as required to preserve the injection in a stable solution.

The antibacterial preparation of the present invention may also be in the form of an infusable or injectable solution containing the above compound [1] or a salt thereof (e.g. lactate) and an acid not producing a precipitate. The acid not producing a precipitate includes, for example, lactic acid, methanesulfonic acid, propionic acid, hydrochloric acid, succinic acid, and the like, preferably lactic acid. In case of using lactic acid, the acid is usually used in an amount of from about 0.1 to 10 % by weight, preferably from about 0.5 to 2 % by weight, based on the weight of the above infusable or injectable solution. In case of using an acid other than lactic acid, the acid is usually used in an amount of from about 0.05 to 4 % by weight, preferably from about 0.3 to 2 % by weight, based on the weight of the above solution. The above infusable or injectable solution may optionally be added with conventional additives, which includes, for example, a thickener, an absorption promoter or inhibitor, a crystallization inhibitor, a complex-forming agent, an antioxidant, an isotonicity-giving agent, or a hydrating agent, and the like. The pH of the solution can properly be adjusted by adding an alkali such as sodium hydroxide, and is usually adjusted within the range of from 2.5 to 7. The infusable or injectable solution thus prepared has an excellent stability, and can be stored and preserved for a long time while retaining the solution state.

The active compounds [1] or salts thereof may be contained in any amount in the preparations, and are usually contained in an amount of from 1 to 70 % by weight based on the whole weight of the preparations.

The pharmaceutical preparations of the present invention can be administered in any methods. Suitable method for administration may be selected in accordance with the preparation form, age and sex of patients, severity of the diseases, and the like. For instance, tablets, pills, solutions, suspensions, emulsions, granules and capsules are administered in oral route. In case of injection, it is administered intravenously in a single form or together with an auxiliary liquid such as glucose or amino acid solution. The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of patients, severity of the diseases, and the like, usually in the range of about 0.2 to 100 mg of the active compound [1] or a salt thereof per 1 kg body weight of the patient per day. The preparation is usually administered by dividing into 2 to 4 times per day.

The present invention is illustrated by the following Reference Examples, Examples, Experiments and Preparations. It is to be understood that the present invention is not limited to these Examples or Experiments and various changes and modifications can be made without departing from the scope and spirit of the present invention.

Reference Example 1

To a solution of 1-cyclopropyl-6-fluoro-7-bromo-5-methyl-1,4-dihydro-4-oxoquinoline-3-carboxylic acid (0.58 g) in N-methyl-2-pyrrolidone (5 ml) is added 3-methylpiperazine (0.65 g), and the mixture is heated at 90° C. for 20 minutes. After the solvent is distilled off under reduced pressure, ethanol is added to the residue, and the crystals are separated by filtration and are recrystallized from ethyl acetate-ethanol to give 1-cyclopropyl-6-fluoro-7-(3-methyl-1-piperazinyl)-5-methyl-1,4-dihydro-4-oxoquinoline-3-carboxylic acid (310 mg), as white powdery crystals, m.p. 206°–208° C.

Reference Example 2

In the same manner as described in Reference Example 1, the following compound is prepared by using an appropriate starting materials.

7-(1-Piperazinyl)-1-cyclopropyl-6-fluoro-5-methyl-1,4-dihydro-4-oxoquinoline-3-carboxylic acid, m.p. 231°–233° C., white powdery crystals (recrystallized from dimethylfomamide)

Reference Example 3

1-Cyclopropyl-6-fluoro-7-(3-methyl-1-piperazinyl)5-methyl-1,4-dihydro-4-oxoquinoline-3-carboxylic acid (8.0 g) is added to methanol (450 ml), and thereto is added gradually sodium borohydride (3.4 g) with stirring under ice cooling. The mixture is stirred at room temperature for one hour. After the reaction is finished, the reaction mixture is adjusted to about pH 1 with conc. hydrochloric acid and then refluxed for 30 minutes, and thereafter methanol is distilled off under reduced pressure. To the resulting residue is added water, and the mixture is made weakly alkaline with saturated aqueous sodium hydrogen carbonate solution and extracted with chloroform. The chloroform layer is dried over sodium sulfate, and chloroform is distilled off. The resulting residue is purified with silica gel column chromatography (eluent, chloroform → chloroform : methanol = 50 : 1) ane then recrystallized from diethyl ether to give 1-cyclopropyl-6-fluoro-7-(3-methyl-1-piperazinyl)-5-methyl-4-oxo-1,2,3,4-tetrahydroquinoline (6.3 g) as yellow prisms, m.p. 98°–100° C.

Reference Example 4

In the same manner as described in Reference Example 3, the following compound is prepared by using appropriate starting materials.

1-Cyclopropyl-6-fluoro-7-(1-piperazinyl)-5-methyl-4-oxo-1,2,3,4-tetrahydroquinoline, m.p. 113°–115° C., yellow particulate crystals (recrystallized from diethyl ether).

Reference Example 5

1-Cyclopropyl-6-fluoro-7-(3-methyl-1-piperazinyl)5-methyl-4-oxo-1,2,3,4-tetrahydroquinoline (5.7 g) is dissolved in dichloromethane (200 ml) and thereto is added gradually sodium methylate (6.8 g) and further added dropwise a solution of ethyl formate (9.3 g) in dichloromethane (100 ml). The mixture is stirred at room temperature for one hour and then refluxed for one hour. After cooling, the reaction mixture is washed with water (200 ml) and dilute aqueous sodium hydroxide solution (200 ml) and extracted. The aqueous layer is taken and is made weakly acidic with diluted hydrochloric acid and extracted with dichloromethane. The extract is washed with water, dried and then dichloromethane is distilled off. The resulting residue is purified by silica gel column chromatography (eluent, chloroform) and recrystallized from diethyl ether - isopropanol to give 1-cyclopropyl-6-fluoro-7-(4-formyl-3-methyl-1-piperazinyl)-5-methyl-4-oxo-3-formyl1,2,3,4-tetrahydroquinoline (4.4 g) as yellow powdery crystals, m.p. 148°–150° C.

Reference Example 6

In the same manner as described in Reference Example 5, the following compound is prepared by using appropriate starting materials.

1-Cyclopropyl-6-fluoro-7-(4-formyl-1-piperazinyl)-5-methyl-4-oxo-3-formyl-1,2,3,4-tetrahydroquinoline, m.p. 139°–141° C., yellowish red particulate crystals.

EXAMPLE 1

1-Cyclopropyl-6-fluoro-7-(4-formyl-3-methyl-1-piperazinyl)-5-methyl-4-oxo-3-formyl-1,2,3,4-tetrahydroquinoline (4.0 g) is dissolved in methanol (150 ml) and thereto is added manganese dioxide (9.3 g), and the mixture is stirred at room temperature for 2 hours. After removing manganese dioxide by filtration with celite, the filtrate is concentrated, and the resulting residue is recrystallized from ethanol to give 1-cyclopropyl-6-fluoro-7-(4-formyl-3 -methyl-1-piperazinyl)-5-methyl-3-formyl-1,4-dihydro-4oxoquinoline (3.9 g), as pale yellow powdery crystals, m.p. 258°–260° C.

EXAMPLE 2

In the same manner as described in Example 1, the following compound is prepared by using appropriate starting materials.

1-Cyclopropyl-6fluoro-7-(4-formyl-1-piperazinyl)-5-methyl-3-formyl-1,4-dihydro-4-oxoquinoline, m.p. 293°–295° C., yellow powdery crystals (recrystallized from ethanol).

EXAMPLE 3

To 1-cyclopropyl-6-fluoro-7-(4-formyl-1-piperazinyl)-5-methyl-3-formyl-1,4-dihydro-4-oxoquinoline (1.2 g) is added 3N hydrochloric acid (15 ml) and the mixture is refluxed for 1 hour. After distilling off hydrochloric acid under reduced pressure, water is added to the resulting residue. The mixture is made weakly alkaline with saturated aqueous sodium hydrogen carbonate solution and extracted with chloroform. The chloroform layer is washed with water, dried over sodium sulfate, and the chloroform is distilled off under reduced pressure. The resulting residue is purified by silica gel column chromatography (eluent, chloroform → chloroform : methanol =50 : 1) and recrystallized from ethanol to give 1-cyclopropyl-6-fluoro-7-(1-piperazinyl)-5-methyl-3-formyl-1,4-dihydro-4oxoquinoline (0.57 g), as pale yellow powdery crystals, m.p. 21020 –213° C. (dec.).

EXAMPLE 4

In the same manner as described in Example 3, the following compound is prepared by using appropriate starting materials.

1-Cyclopropyl-6-fluoro-7-(3-methyl-1-piperazinyl)-5-methyl-3-formyl-1,4-dihydro-4-oxoquinoline, m.p. 191°–194° C., white powdery crystals (recrystallized from isopropanol)

Preparation 1

An injection preparation is prepared from the following components.

| Components | Amount |
| --- | --- |
| 7-(3-Methyl-1-piperazinyl)-1-cyclopropyl-6-fluoro-5-methyl-3-formyl-1,4-dihydro-4-oxoquinoline | 200 mg |
| Glucose | 250 mg |
| Distilled water for injection | q.s. |
| Totally | 5 ml |

7-(3-methyl-1-piperazinyl)-1-cyclopropyl-6-fluoro5-methyl-3-formyl-1,4-dihydro-4-oxoquinoline and glucose are dissolved in distilled water for injection, and the solution is added to a 5 ml ampoule, which is purged with nitrogen gas and then subjected to sterilization at 121° C. for 15 minutes to give an injection preparation.

Preparation 2

Film coated tablets are prepared from the following components.

| Components | Amount |
| --- | --- |
| 7-(1-Piperazinyl)-1-cyclopropyl-6-fluoro-5-methyl-3-formyl-1,4-dihydro-4-oxoquinoline | 100 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| TC-5 (tradename of hydroxypropyl methylcellulose, manufactured by The Shin-Etsu Chemical Co., Ltd., Japan) | 10 g |
| Polyethylene glycol 6000 | 3 g |
| Castor oil | 40 g |
| Ethanol | 40 g |

7-(1-Piperazinyl)-1-cyclopropyl-6-fluoro-5-methyl-3-formyl-1,4-dihydro-4-oxoquinoline, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

Preparation 3

An ointment is prepared from the following components.

| Components | Amount |
| --- | --- |
| 7-(3-Methyl-1-piperazinyl)-1-cyclopropyl-6-fluoro-5-methyl-3-formyl-1,4-dihydro-4-oxoquioline | 2 g |
| Purified lanolin | 5 g |
| Bleached beeswax | 5 g |

| Components | Amount |
| --- | --- |
| White vaseline | 88 g |
| Totally | 100 g |

Bleached beeswax is made liquid by heating, and thereto are added 7-(3-methyl-1-piperazinyl)-1-cyclopropyl-6-fluoro-5-methyl-3-formyl-1,4-dihydro-4-oxoquinoline, purified lanolin and while vaseline, and the mixture is heated until it becomes liquid. The mixture is stirred until it is solidified to give an ointment.

Experiment (Antimicrobial activity in vivo)

The antimicrobial activity of the test compound as mentioned below was tested by measuring the 50 % effective dose ($ED_{50}$) in mice as follows.

*Escherichia coli* No. 29 strain was cultured in a nutrient medium at 37° C., and the culture broth was diluted with the same medium and thereto was added an equivolume of 6 % mucin solution to prepare a cell solution.

The cell solution thus prepared (0.5 ml) (*e. coli* cells; $10^5$–$10^6$ cells/mouse) was intraperitoneally administered to mice (10 mice per group). One hour after the injection, the test compound was orally administered to the mice, and the mice were observed for one week. From the number of dead mice and the survival mice, the 50 % effective dose ($ED_{50}$) of the test compound was calculated by Probit method.

The result was as follows.

| Test compound | $ED_{50}$ (mg/kg) |
| --- | --- |
| 7-(3-Methyl-1-piperazinyl)-1-cyclopropyl-6-fluoro-5-methyl-3-formyl-1,4-dihydro-4-oxo-quinoline | 0.331 |

What is claimed is:

1. A compound of the formula:

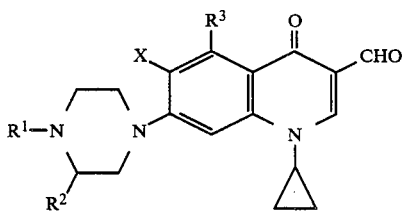

wherein $R^1$ is hydrogen atom or a lower alkanoyl group, $R^2$ is hydrogen atom or a lower alkyl group, $R^3$ is a lower alkyl group, and X is a halogen atom, or a pharmaceutically acceptable salt thereof.

2. The compound according to claim 1, wherein $R^1$ is hydrogen atom, $R^2$ is hydrogen atom or a $C_1$–$C_6$ alkyl group, and $R^3$ is a $C_1$–$C_6$ alkyl group, or a pharmaceutically acceptable salt thereof.

3. The compound according to claim 1, wherein $R^1$ is a $C_1$–$C_6$ alkanoyl group, $R^2$ is hydrogen atom or a $C_1$–$C_6$ alkyl group, and $R^3$ is a $C_1$–$C_6$ alkyl group, or a pharmaceutically acceptable salt thereof.

4. The compound according to claim 2, wherein $R^2$ is hydrogen atom, or a pharmaceutically acceptable salt thereof.

5. The compound according to claim 2, wherein $R^2$ is a $C_1$–$C_6$ alkyl group, or a pharmaceutically acceptable salt thereof.

6. The compound according to claim 3, wherein $R^2$ is hydrogen atom, or a pharmaceutically acceptable salt thereof.

7. The compound according to claim 3, wherein $R^2$ is a $C_1$–$C_6$ alkyl group, or a pharmaceutically acceptable salt thereof.

8. The compound according to claim 4, wherein $R^3$ is methyl group, or a pharmaceutically acceptable salt thereof.

9. The compound according to claim 5, wherein $R^2$ and $R^3$ are both methyl group, or a pharmaceutically acceptable salt thereof.

10. The compound according to claim 6, wherein $R^3$ is methyl group, or a pharmaceutically acceptable salt thereof.

11. The compound according to claim 7, wherein $R^2$ and $R^3$ are both methyl group, or a pharmaceutically acceptable salt thereof.

12. 1-Cyclopropyl-6-fluoro-7-(1-piperazinyl)-5 methyl-3-formyl-1,4-dihydro-4-oxoquinoline.

13. 1-Cyclopropyl-6-fluoro-7-(3-methyl-1 piperazinyl)-5-methyl-3-formyl-1,4-dihydro-4-oxoquinoline.

14. An antimicrobial composition which comprises as an essential active ingredient an effective amount of a compound as set forth in claim 1 in admixture with a pharmaceutically acceptable carrier or diluent.

15. A composition according to claim 14, wherein the active ingredient is 1-cyclopropyl-6-fluoro-7-(1-piperazinyl)-5-methyl-3-formyl-1,4-dihydro-4-oxoquinoline.

16. A composition according to claim 14, wherein the active ingredient is 1-cyclopropyl-6-fluoro-7-(3-methyl-1-piperazinyl)-5-methyl-3-formyl-1,4-dihydro-4-oxoquinoline.

* * * * *